(12) United States Patent
Li et al.

(10) Patent No.: US 12,325,869 B2
(45) Date of Patent: Jun. 10, 2025

(54) OLIGOSACCHARIDE DEBRANCHING ENZYME MUTANT AND USE THEREOF IN GLUCOSE MOTHER LIQUOR

(71) Applicant: JIANGNAN UNIVERSITY, Wuxi (CN)

(72) Inventors: Zhaofeng Li, Wuxi (CN); Shixia Xi, Wuxi (CN); Zhengbiao Gu, Wuxi (CN); Caiming Li, Wuxi (CN); Xiao Zhang, Wuxi (CN); Zexi Li, Wuxi (CN); Xiaofeng Ban, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 18/634,776

(22) Filed: Apr. 12, 2024

(65) Prior Publication Data
US 2025/0122484 A1 Apr. 17, 2025

Related U.S. Application Data

(63) Continuation of application No. PCT/CN2023/103662, filed on Jun. 29, 2023.

(30) Foreign Application Priority Data

Nov. 28, 2022 (CN) .......................... 202211504329.2

(51) Int. Cl.
| | |
|---|---|
| *C12N 15/67* | (2006.01) |
| *C12N 9/10* | (2006.01) |
| *C12N 9/24* | (2006.01) |
| *C12N 15/70* | (2006.01) |
| *C12P 19/02* | (2006.01) |

(52) U.S. Cl.
CPC ............ *C12N 9/1055* (2013.01); *C12P 19/02* (2013.01); *C12Y 204/0101* (2013.01)

(58) Field of Classification Search
CPC .......... C12N 15/67; C12N 9/24; C12N 15/70; C12N 9/1055; C12N 9/2402; C12P 19/02; C12Y 302/0101
See application file for complete search history.

(56) References Cited

FOREIGN PATENT DOCUMENTS

| | | |
|---|---|---|
| CN | 116064456 A | 5/2023 |
| WO | 0001796 A2 | 1/2000 |

OTHER PUBLICATIONS

Kunihiko Watanabe et al., "Multiple proline substitutions cumulatively thermostabilize Bacillus cereus ATCC7064 oligo-1,6-glucosidase Irrefragable proof supporting the proline rule" Eur. J. Biochem. 226, 277-283 (Dec. 1, 1994).

Peihua Li et al., "Improving beta-glucosidase activity by site-directed mutagenesis" Genomics and Applied Biology, 2016, vol. 35, No. 8, 2083-2091 (Jun. 13, 2016).

*Primary Examiner* — Maryam Monshipouri
(74) *Attorney, Agent, or Firm* — SZDC Law PC

(57) ABSTRACT

The invention provides an oligosaccharide debranching enzyme mutant and use thereof in a glucose mother liquor. The mutant is obtained by mutating valine at position 219 in SEQ ID NO: 1 into alanine. According to oligosaccharide debranching enzyme mutant V219A, a primary mother liquor, a secondary mother liquor, or a tail liquid after chromatographic separation is used as a substrate, the percentage contents of glucose in the products are 99.21% (primary mother liquor), 98.89% (secondary mother liquor) and 97.97% (tail liquid after chromatographic separation) respectively, which are 2.86%, 8.64%, and 28.67% higher than that of glucose obtained with the wild-type oligosaccharide debranching enzyme. Therefore, the mutant V219A obviously improves the percentage content of glucose in the glucose mother liquor, and the scope of application of the mother liquor can be expanded by the high product purity and substrate conversion rate, so the mutant V219A has higher industrial application value.

10 Claims, 3 Drawing Sheets

Specification includes a Sequence Listing.

OLIGOSACCHARIDE DEBRANCHING ENZYME MUTANT AND USE THEREOF IN GLUCOSE MOTHER LIQUOR

This application is a Continuation Application of PCT/CN2023/103662, filed on Jun. 29, 2023, which claims priority to Chinese Patent Application No. 202211504329.2, filed on Nov. 28, 2022, which is incorporated by reference for all purposes as if fully set forth herein.

A Sequence Listing XML file named "10015_0149.xml" created on Apr. 12, 2024, and having a size of 5,073 bytes, is filed concurrently with the specification. The sequence listing contained in the XML file is part of the specification and is herein incorporated by reference in its entirety.

FIELD OF THE INVENTION

The present invention relates to the technical field of enzyme engineering, and particularly to an oligosaccharide debranching enzyme mutant and use thereof in a glucose mother liquor.

DESCRIPTION OF THE RELATED ART

Glucose is an organic compound having a molecular formula of C6H12O6, It is the most widely distributed and important monosaccharide in nature. Glucose is a colorless crystal which is sweet, but not as sweet as sucrose. Glucose is an essential nutrient for metabolism in organisms, and can be easily absorbed into the blood. Therefore, it is often used as a powerful and rapid energy supplement by hospital staff, sports enthusiasts and ordinary people. Medically, glucose can enhance the memory, stimulate the calcium absorption and increase the communication between cells. The growth of microorganisms in fermentation industry needs a suitable ratio of carbon to nitrogen. Glucose, as a carbon source for microorganisms, is a main material in the fermentation medium. In the food industry, fructose can be made from glucose after treatment with an isomerase. Particularly, fructose syrup with 42% fructose is as sweet as sucrose and, has become an important product in sugar industry at present. Glucose is also widely used in industry. It is used as a reducing agent in the dyeing and tanning industry, and also often used as a reducing agent in the mirror-making industry and the silver plating process of thermos bottles. In industry, glucose can also be isomerized into mannose (a raw material for producing mannitol), or sorbitol that can be further used to produce vitamin C for wide use in clinical treatment. 15% mannitol is clinically used as a safe and effective drug to reduce intracranial pressure, to treat brain edema and glaucoma.

Glucose is mainly industrially produced with starch by acid method, acid-enzyme method or double enzyme method, followed by decolorizing, ion exchange, concentration, crystallization, separation, and drying. In the production process of crystalline glucose, glucose is usually crystallized by cooling. The remaining solution after crystals are separated from the crystal slurry by centrifugation is called glucose mother liquor after crystallization. About 200,000 tons of glucose mother liquor is produced per 1 million tons of crystalline glucose. The medium-purity molasses produced by primary separation is fed back at a certain ratio, and the mother liquor is subjected to primary and secondary crystallization in some enterprises, to produce a secondary and tertiary mother liquor. The glucose mother liquor generally has a dry DS value of about 55%, including about 78% of glucose, about 13% of disaccharides, and about 10% of trisaccharides and higher saccharider. In addition to the largely present glucose, a large amount of isomaltooligosaccharide is contained. In the process of crystallization, a large volume of mother liquor is produced, which is difficult to be formed into a standardized product, and mainly sold. Because of the large sales and low price, the economical benefit of crystallized sugar is affected. Especially in the off-season of mother liquor sales, the inventory pressure of mother liquor increases, which affects the healthy development of the industry chain of the recycling economy focusing on deep processing of corns to some extent. At present, the mother liquor can not only be sold at a low price directly, but also treated through other routes, to improve the utilization value of the mother liquor. This is an urgent problem to be solved to ensure the healthy development of the industry chain of the recycling economy focusing on deep processing of corns.

Because there are still many linear maltooligosaccharide and isomaltooligosaccharides with small molecular weight in the glucose mother liquor, Treating the mother liquor with an enzyme which can catalyze the short-chain substrates to generate glucose is a method to further improve the value of the glucose mother liquor. However, the naturally occurring enzymes cannot catalyze the linear maltooligosaccharide and isomaltooligosaccharide at the same time. Therefore, the small molecular oligosaccharide in the mother liquor cannot be effectively converted into glucose. Accordingly, it is imperative to develop an enzyme with two catalytic functions.

The oligosaccharide debranching enzyme (Oligo-1,6-Glucosidase; EC 2.4.1.10) is a hydrolase belonging to the glycoside hydrolase family 13 (GH13), which can specifically catalyze the cleavage of α-1,6-glycosidic bonds in oligosaccharide molecules to produce glucose. However, it is difficult for wild-type oligosaccharide debranching enzyme to catalyze the residual maltooligosaccharides and isomaltooligosaccharides in the mother liquor to meet the requirement of increasing the glucose yield in industry. Therefore, it is an effective strategy to improve the glucose yield in industry by engineering the wide-type oligosaccharide debranching enzyme to expand the substrate range and broaden the scope of application.

SUMMARY OF THE INVENTION

To solve the above problems, an oligosaccharide debranching enzyme derived from *Paenibacillus* sp. STB16 is mutated in the present invention, to obtain a mutant V219A that can catalyze both linear maltooligosaccharide and isomaltooligosaccharide. V219A has additional catalytic ability for linear maltooligosaccharide on the basis of original catalytic ability for isomaltooligosaccharide. V219A can catalyze the residual maltooligosaccharide and isomaltooligosaccharide in a mother liquor (a primary mother liquor, a secondary mother liquor, or a tail liquor after separation) to give a percentage content of glucose in the product up to 99.21%, 98.89% and 97.97% respectively, Therefore, V219A is more suitable for industrial production.

A first object of the present invention is to provide an oligosaccharide debranching enzyme mutant, obtained by mutating valine at position 219 in an amino acid sequence as shown in SEQ ID NO: 1 into alanine. Particularly, the amino acid sequence of the wide type is shown below:

MLLFPFESRSRSIPTGGWQMKRAWWKESVVYQIYPRSFQDSNGDG

IGDIPGIVSRLDYLQELGVDVVWLCPVYDSPNDDNGYDIRDYRRI

MDEFGTLEDWERLLEDLHARGMKLIMDLVVNHSSDEHAWFSESRK

SRDGEHRDYYIWRDGKGGAEPNNWSSFFSGSAWKYDGETDQYYLH

LFSSKQPDLNWENGKVRREVYNMMAWWLDKGIDGFRMDVINLISK

VPGLPDAPGEGRYRSGADYFMNGPRVHEYLQEMNREVLSRYDIMT

VGETPGVTPEQAALYVGEDRGELNMVFQFEHMDIDSGPGGKWDVQ

PWRLTDFKRVMGKWQRELQDRGWNSLYLNNHDQPRMVSRFGDDKN

FRKQSAKMLGTLLHTLQGTPYIYQGEELGMTNVRFGSIEDYRDIE

TLNMYKEATGAGRPAEAVMASVYSKGRDNARTPMQWDGSAHGGFT

TGTPWIASNPNYTEINAEDARRDPDSIFHYYRRLIALRKQHDVIV

YGRYEALLEEDERIYAYTRMLDGERLLVVLNFFGEEADCSLPEKI

RFESAEPLIGNYGNGADRDWRSLKLRPYEALVLRLQG.

A second object of the present invention is to provide a gene encoding the oligosaccharide debranching enzyme mutant.

Preferably, the gene encoding the oligosaccharide debranching enzyme mutant has a nucleotide sequence as shown in SEQ ID NO: 2. Specifically, the sequence is as shown below:

ATGCTTCTATTTCCATTTGAGAGCAGGAGCAGATCCATACCGACA

GGAGGCTGGCAGATGAAGCGAGCATGGTGGAAGGAAAGCGTCGTC

TATCAGATTTATCCCCGCAGCTTCCAGGACAGCAACGGAGACGGC

ATCGGCGACATCCCGGGAATCGTTTCCCGGCTGGATTATTTGCAG

GAGCTCGGCGTGGATGTCGTCTGGCTCTGTCCCGTCTATGACTCC

CCCAATGACGACAACGGCTACGATATTCGCGACTATCGGCGCATC

ATGGACGAATTCGGCACGCTAGAGGACTGGGAAAGGCTGCTGGAG

GATCTCCATGCCCGCGGCATGAAGCTGATCATGGACCTCGTCGTG

AACCACAGCTCGGACGAGCATGCCTGGTTCTCGGAATCCCGCAAG

TCCCGGGACGGCGAGCATCGCGATTACTATATTTGGCGGGACGGC

AAGGGCGGAGCGGAGCCGAACAACTGGTCGAGCTTCTTCAGCGGC

TCCGCATGGAAATACGATGGGGAGACGGATCAGTATTATCTGCAT

CTGTTCTCCTCCAAGCAGCCCGATCTCAACTGGGAGAACGGGAAG

GTCCGCCGCGAGGTGTACAATATGATGGCCTGGTGGCTGGACAAA

GGCATCGACGGCTTCCGTATGGACGCCATCAACCTGATCTCCAAG

GTTCCCGGACTGCCGGACGCCCCCGGAGAAGGACGGTACCGTTCC

GGCGCCGATTATTTCATGAACGGCCCGAGGGTGCATGAGTATTTG

CAGGAGATGAACCGCGAGGTGCTGTCCCGCTACGACATCATGACC

GTGGGGGAGACGCCGGGCGTGACGCCGGAGCAGGCGGCTCTGTAC

GTCGGCGAGGACCGCGGAGAGCTGAACATGGTGTTTCAGTTCGAG

CACATGGACATCGATTCCGGACCTGGCGGCAAATGGGACGTGCAG

CCTTGGAGGCTGACGGATTTCAAGCGCGTCATGGGCAAATGGCAG

CGGGAGCTGCAGGACAGGGGCTGGAACAGCCTGTACCTGAACAAT

CACGACCAGCCGCGGATGGTGTCCCGCTTCGGCGATGACAAGAAC

TTCCGCAAGCAGTCCGCCAAAATGCTCGGCACGCTGCTGCACACG

CTGCAGGGAACGCCCTACATCTATCAGGGCGAGGAGCTCGGCATG

ACCAACGTCCGGTTCGGCTCCATCGAGGACTACCGGGATATCGAG

ACGCTGAACATGTACAAGGAAGCGACCGGGGCCGGACGTCCCGCG

GAGGCTGTCATGGCTTCCGTCTACAGCAAAGGAAGGGACAATGCC

CGCACGCCTATGCAGTGGGACGGATCCGCTCACGGAGGCTTCACG

ACCGGCACGCCGTGGATCGCGTCCAACCCCAATTACACGGAGATC

AATGCGGAGGACGCCCGGAGAGATCCGGATTCCATCTTCCACTAC

TATCGCCGGCTCATCGCGCTCCGCAAGCAGCATGACGTCATCGTC

TACGGCAGGTACGAGGCGCTGCTAGAGGAGGACGAGCGGATCTAT

GCGTATACGCGCATGCTGGATGGAGAGCGCCTGCTTGTCGTGCTG

AACTTCTTTGGAGAGGAAGCCGACTGCAGCTTGCCGGAGAAGATA

CGATTCGAGAGCGCCGAGCCGCTCATCGGCAATTACGGGAATGGA

GCGGATAGAGATTGGCGCAGCCTGAAGCTTCGGCCTTATGAGGCG

CTCGTCCTGCGCTTGCAGGGCTGA.

A third object of the present invention is to provide a recombinant plasmid carrying the gene.

Preferably, the vector of the recombinant plasmid includes, but is not limited to, pET-28a, pET-28b, and so on.

A fourth object of the present invention is to provide a host cell expressing the oligosaccharide debranching enzyme mutant.

Preferably, the host cell is bacterial, fungal, plant or animal cells.

Preferably, the bacterium is *E. coli*, preferably *E. coli* BL21 (DE3).

A fifth object of the present invention is to provide use of the oligosaccharide debranching enzyme mutant, the gene, the recombinant plasmid, or the host cell in the hydrolysis of an oligosaccharide or the production of glucose.

Preferably, glucose is produced with the oligosaccharide as a substrate, and the oligosaccharide debranching enzyme mutant, or a whole cell or a preparation including the mutant as a catalyst.

Preferably, the oligosaccharide includes linear maltooligosaccharide or isomaltooligosaccharide.

A sixth object of the present invention is to provide a method for regenerating glucose with a glucose mother liquor. The method includes treating the glucose mother liquor with the oligosaccharide debranching enzyme mutant, or a whole cell or a preparation including the mutant. In the present invention, unless otherwise indicated, the glucose mother liquor refers to a residual liquid from which crystalline glucose is extracted one or more times, for example, primary mother liquor, secondary mother liquor, tertiary mother liquor, or tail liquid after separation.

Preferably, in the method, the glucose mother liquor is used as a substrate, the oligosaccharide debranching enzyme mutant is added in an amount of 5-10 U/g, and the reaction is carried at pH 5.0-7.0 and 40-60° C. (in the following examples, the pH is 6.0, and the temperature is 50° C.).

As compared with the prior art, the invention has the following beneficial effects:

(1) In the present invention, an isomaltose debranching enzyme derived from B *Paenibacillus* sp. STB16 is mutated, such that the isomaltose debranching enzyme unable to catalyze the linear maltooligosaccharide is engineered into an oligosaccharide debranching enzyme having catalytic ability for linear maltooligosaccharide, thus expanding the substrate range of the enzyme. The variant performs well in the preparation of glucose from the mother liquor after the target oligosaccharide is separated in the oligosaccharide production.

(2) The oligosaccharide debranching enzyme mutant according to the present invention can efficiently hydrolyze oligosaccharides to produce glucose. When panose is used as substrate, the oligosaccharide debranching enzyme mutant V219A can convert panose into glucose with a conversion rate of 100%. When a primary mother liquor, a secondary mother liquor, or a tail liquid after chromatographic separation is used as a substrate, the percentage contents of glucose in the products obtained with the oligosaccharide debranching enzyme mutant V219A are 99.21% (primary mother liquor), 98.89% (secondary mother liquor) and 97.97% (tail liquid after chromatographic separation) respectively, which are 2.86%, 8.64%, and 28.67% higher than the percentage content of glucose obtained with the wild-type oligosaccharide debranching enzyme. Considering the percentage content of glucose (93.97%, 82.72%, and 52.07%) in the mother liquor, the mutant V219A significantly improves the percentage content of glucose in the glucose mother liquor and the tail liquid after chromatographic separation. Particularly, the percentage content of glucose in the tail liquid after chromatographic separation is improved by 45.90%. The scope of application of the mother liquor can be expanded by the high product purity and substrate conversion rate, so the mutant V219A has higher industrial application value.

DETAILED DESCRIPTION OF THE PREFERRED EMBODIMENTS

Figure 1:
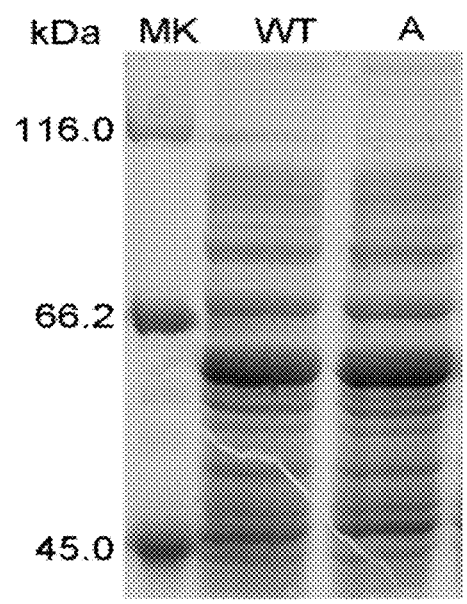
FIG. 1 shows the SDS-PAGE analysis of the oligosaccharide debranching enzyme.

The present invention will be further described below with reference to the accompanying drawings and specific examples, so that those skilled in the art can better understand and implement the present invention; however, the present invention is not limited thereto.

Detection methods involved:
p-nitrobenzene-α-d-glucopyranoside (pNPG) is used as the substrate. The reaction mixture includes 150 μL of a 500 mM phosphate buffer (pH 6.0), 800 μL of 10 mM pNPG and 50 μL of enzyme. After incubation at 50° C. for 5 min, 1 mL of 1 M sodium carbonate is added, to stop the reaction. The standard curve is measured and calibrated by measuring the increase of absorbance at 410 nm of the released p-nitrobenzene (pNP). One unit (U) of hydrolysis activity is defined as the amount of enzyme required to produce 1 μmol pNP per minute under the experimental conditions.

The contents of various components in the product from enzymatic catalysis of panose are analyzed by high performance anion exchange chromatography (HPAEC-PAD). Analytical conditions: chromatographic column CarboPac PA 200, mobile phase: 0.25 M NaOH, 1 M NaAc and ultrapure water, flow rate: 0.5 mL/min, column temperature: 35° C., and injection volume: 10 μL.

The contents of various components in the product from enzymatic catalysis of the glucose mother liquor are analyzed by high performance anion exchange chromatography (HPLC). Analytical conditions: chromatographic column: Hypersil APS2, mobile phase: 70% (V/V) acetonitrile and ultrapure water, flow rate: 1.0 mL/min, column temperature: 30° C., and injection volume: 10 μL.

Example 1. Production of Gene Sequence Encoding Oligosaccharide Debranching Enzyme Mutant The expression vector oga/pET-28a was used as a template, the complementary primer chains needed for the experiment were designed (see Table 1), and the primers were synthesized by Genewiz Biotech Corp. Site-directed mutation was carried out according to the method in the instructions for use of STAR Primer GXL kit of TaKaRa company. The PCR reaction system were based on the conditions set in the instructions for use of STAR Primer kit: 5×PrimeSTAR Buffer ($Mg^{2+}$ Plus) 10 μL, template DNA 1 μL, forward and reverse primers (10 μM) each 1 μL, PrimeSTAR HS DNA Polymerase (2.5 U/μL) 0.5 μL, dNTPs (2.5 mM) 4 μL, and ultrapure water 32.5 μL. PCR amplification conditions: predenaturation at 98° C. for 3 min, 35 cycles of denaturation at 98° C. for 30 s, annealing at 60° C. for 30 s, and extension at 68° C. for 3 min, and incubation at 68° C. for 5 min.

TABLE 1

| Introduction of mutation sites to oligosaccharide debranching enzyme | |
|---|---|
| Primers: | Primer sequence (5'-3')[1] |
| V219A-For | GACGGCTTCCGTATG GACGCCATCAACCT |
| V219A-Rev | CTTGGAGATCAGGTT GATGGCGTCCATAC |

Note:
[1]The underlined bases correspond to the correspondingly mutated amino acids.

Example 2. Construction of Genetically Engineered Strain (1) At 37° C., the PCR product obtained in Example 1 was treated with Dpn I for 2 h, and then the treated PCR product was transformed into *E. coli* JM109. The transformed *E. coli* JM109 was coated onto LB agar medium containing 100 μg/mL kanamycin, and cultured overnight for 12 h in an incubator at 37° C. Single colonies were picked up and inoculated into LB liquid medium containing 100 μg/mL kanamycin, and cultured overnight at 37° C. and 200 r/min. The plasmids were extracted, identified and sequenced according to the instruction for use of the plasmid extraction kit.

(2) The gene encoding the oligosaccharide debranching enzyme mutant obtained in Example 1 was ligated to the pET-28a plasmid vector by homologous recombination. Ligation system: purified PCR fragments of gene encoding oligosaccharide debranching enzyme mutant (50 ng/μL) 1 μL, PCR fragments of purified pET-28a plasmid vector (50 ng/μL) 2 μL, 5×CE II Buffer 4 μL, Exnase II 2 μL, ddH$_2$O 11 μL. The conditions for homologous recombination include incubation at 37° C. for 30 min. Then, the recombination product was transformed into *E. coli* JM109, and the cells were coated onto LB agar medium containing 100 μg/mL kanamycin, and cultured overnight for 12 h in an incubator at 37° C. Single colonies were picked up and inoculated into LB liquid medium containing 100 μg/mL kanamycin, and cultured overnight at 37° C. and 200 r/min. The plasmids were extracted, identified and sequenced according to the instruction for use of the plasmid extraction kit. The plasmid sequenced to be correct and containing the gene encoding the oligosaccharide debranching enzyme mutant was transformed into the expression host competent *E. coli* BL21 (DE 3) cells. Finally, the genetically engineered strain *E. coli* BL21 (DE 3) (pET-28a/oga) was obtained.

Example 3. Expression of Oligosaccharide Debranching Enzyme Mutant (1) Activation and culture of host strain: The genetically engineered strain *E. coli* BL21 containing the expression plasmid pET-28a/oga obtained in Example 2 was inoculated onto LB solid medium by streak plate method, and then cultured overnight in a constant-temperature incubator at 37° C. The positive single colony was picked up and inoculated in a 250 ml conical flask containing 50 mL LB liquid culture medium. Kanamycin with a final concentration of 100 μg/mL was added before inoculation. The conical flask was placed in a rotary shaker at 200 r/min and cultured at 37° C. for 12 h.

(2) Fermentation culture: The activated seed culture was inoculated into a 250 mL conical flask with 50 ml fermentation medium in an inoculation amount of 4% (v/v), and cultured in a rotary shaker for 48 h (at a rotation speed of 200 r/min). Kanamycin with a final concentration of 100 μg/mL L was added before inoculation. After fermentation, the fermentation broth was centrifuged at 4° C. and 10,000×g for 15 min, and the cells were collected. The cells were suspended in 50 mM sodium acetate buffer, ultrasonically homogenized for 30 min, and then centrifuged at 10,000×g for 15 min to obtain a supernatant that is the crude enzyme solution.

Example 4. Analysis of Products Obtained with Oligosaccharide Debranching Enzyme Mutant 1 mg/mL panose (pH 6.0) was prepared, the wide type (having an amino acid sequence as shown in SEQ ID NO: 1) or the oligosaccharide debranching enzyme mutant V219A was added in an amount of 5 U/g, and the reaction was continued for 24 hrs at 50° C. After the reaction, the enzyme was inactivated by standing in a boiling water bath. The reaction solution was centrifuged at 10,000×g for 5 min, diluted by a certain factor and filtered through a 0.22 m needle filter. Qualitative and quantitative analysis were carried out with G1-G7 over a certain gradient of concentrations mixed with the standard as a control.

Figure 2:
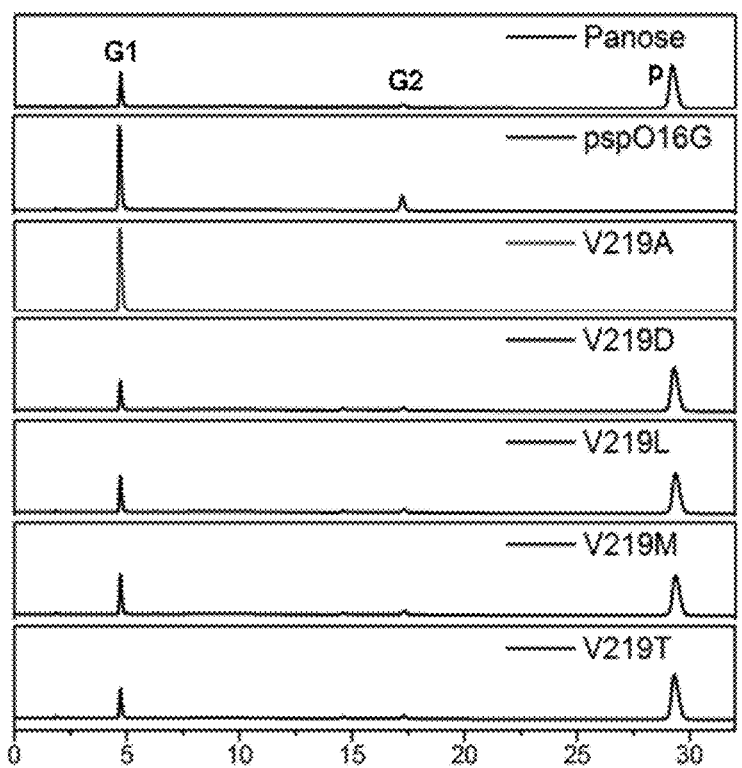
FIG. 2 shows a HPAEC-PAD curve obtained when the oligosaccharide debranching enzyme acts on 1 mg/mL panose.
Figure 3:
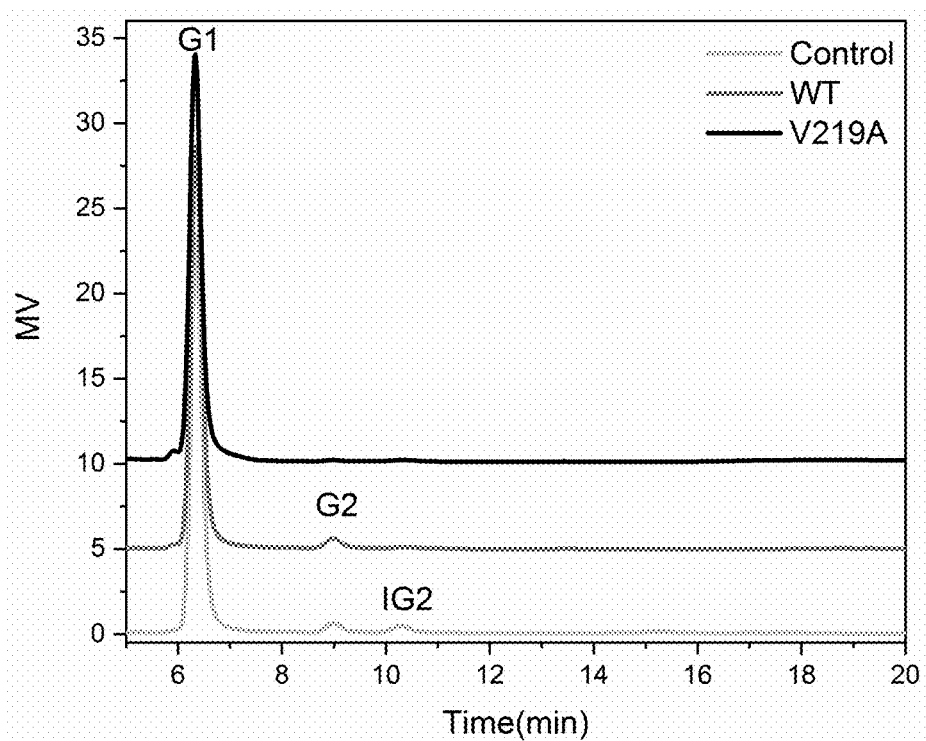
FIG. 3 is a HPLC curve obtained when the oligosaccharide debranching enzyme acts on 5% (w/w) primary mother liquor.
Figure 4:
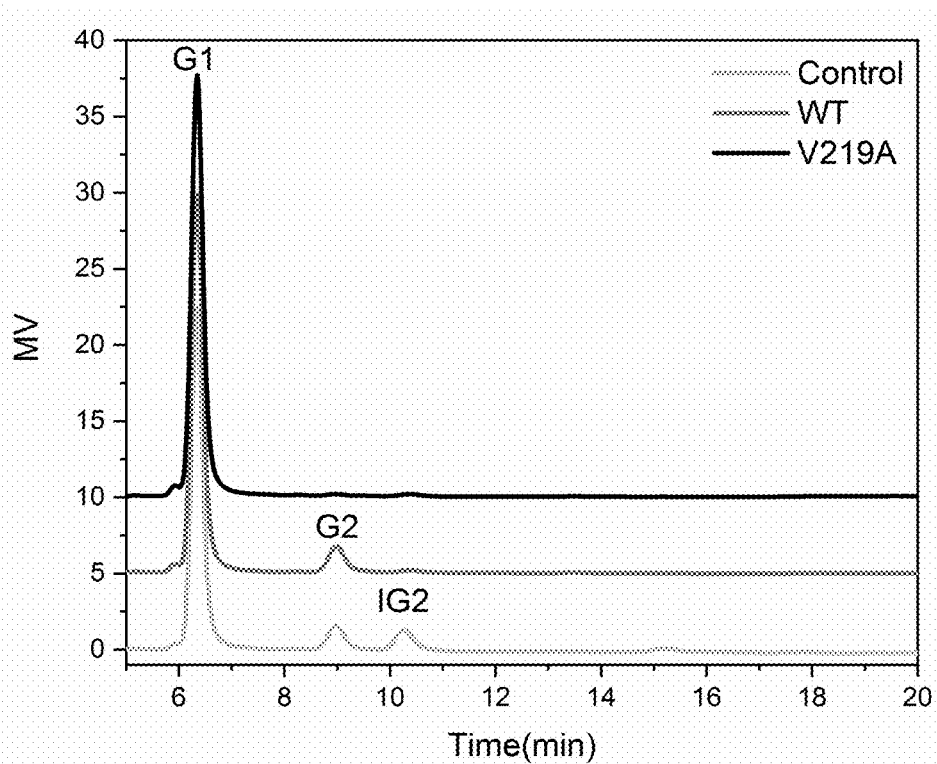
FIG. 4 is a HPLC curve obtained when the oligosaccharide debranching enzyme acts on 5% (w/w) secondary mother liquor.
Figure 5:
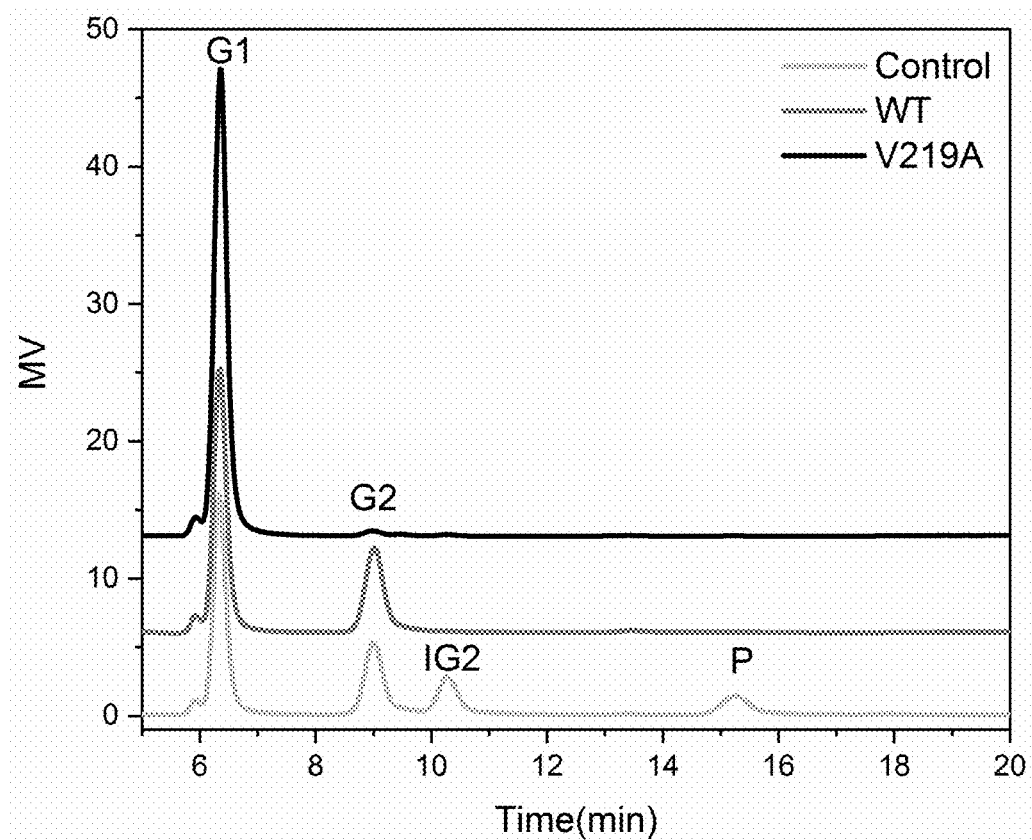
FIG. 5 is a HPLC curve obtained when the oligosaccharide debranching enzyme acts on 5% (w/w) tail liquid after chromatographic separation.

The results of product analysis are shown in FIG. 2. The wild type catalyzes the hydrolysis of panose to glucose and maltose, and the oligosaccharide debranching enzyme mutant catalyzes the hydrolysis of panose to glucose only. The rate of conversion of panose to glucose by the oligosaccharide mutant is 100%. Compared with the wild type, the conversion ability of the oligosaccharide mutant is significantly improved.

TABLE 2

| Analysis of products obtained with with oligosaccharide debranching enzyme | | |
|---|---|---|
| Components in the product (%) | Wild type | V219A |
| G1 | 60 | 100 |
| G2 | 33 | 0 |

Note:
G1 and G2 represent glucose and maltose respectively.

Example 5. Production of Glucose Through Hydrolysis of Primary Mother Liquor by Oligosaccharide Debranching Enzyme 5% (w/w) primary mother liquor was prepared, adjusted to pH 6.0, and allowed to stand in a water bath at 50° C. for 15 min. The stirring speed was 300 r/min. The oligosaccharide debranching enzyme or the mutant V219A was added at a dosage of 10 U/g dry starch, and the reaction was timed. 24 hrs after reaction, the product was determined by HPLC after centrifugation, membrane filtration and dilution. The percentage contents of various sugar components are shown in Table 3. The percentage content of glucose in the hydrolysate of wild-type oligosaccharide debranching enzyme is 96.35%. The percentage content of glucose in the hydrolysate of the variant V219A is 99.21%, and increased by 2.86%.

TABLE 3

| Analysis of products obtained by treatment of primary mother liquor with oligosaccharide debranching enzyme | | | |
|---|---|---|---|
| Components product | in Primary mother liquor (%) | Wide type (%) | V219A (%) |
| G1 | 93.97 | 96.35 | 99.21 |
| G2 | 3.08 | 3.26 | 0.28 |
| IG2 | 2.50 | 0.39 | 0.51 |
| G3 | — | — | — |
| P | 0.45 | — | — |
| IG3 | — | — | — |

Note:
G1 to G4 represents glucose, maltose, linear maltotriose, and linear maltotetraose respectively; IG2 to IG3 represents isomaltose, and isomaltotriose respectively; and P represents panose.

Example 6. Production of Glucose Through Hydrolysis of Secondary Mother Liquor by Oligosaccharide Debranching Enzyme 20% (w/w) secondary mother liquor was prepared, adjusted to pH 6.0, and allowed to stand in a water bath at 50° C. for 15 min. The stirring speed was 300 r/min. The oligosaccharide debranching enzyme or the mutant V219A was added at a dosage of 10 U/g dry starch, and the reaction was timed. 24 hrs after reaction, the product was determined by HPLC after centrifugation, membrane filtration and dilution. The percentage contents of various sugar components are shown in Table 4. The percentage content of glucose in the hydrolysate of wild-type oligosaccharide debranching enzyme is 90.25%. The percentage content of glucose in the hydrolysate of the variant V219A is 98.89%, and increased by 8.64%.

TABLE 4

Analysis of products obtained by treatment of secondary mother liquor with oligosaccharide debranching enzyme

| Components product | in Secondary mother liquor (%) | Wide type (%) | V219A (%) |
|---|---|---|---|
| G1 | 82.72 | 90.25 | 98.89 |
| G2 | 7.99 | 8.83 | 0.36 |
| IG2 | 7.20 | 0.92 | 0.75 |
| G3 | — | — | — |
| P | 1.84 | — | — |
| IG3 | 0.25 | — | — |

Note:
G1 to G3 represents glucose, maltose, and linear maltotriose respectively; IG2 to IG3 represents isomaltose, and isomaltotriose respectively; and P represents panose.

Example 7. Production of Glucose Through Hydrolysis of Tertiary Mother Liquor by Oligosaccharide Debranching Enzyme 20% (w/w) tail liquid after chromatographic separation was prepared, adjusted to pH 6.0, and allowed to stand in a water bath at 50° C. for 15 min. The stirring speed was 300 r/min. The oligosaccharide debranching enzyme or the mutant V219A was added at a dosage of 10 U/g dry starch, and the reaction was timed. 24 hrs after reaction, the product was determined by HPLC after centrifugation, membrane filtration and dilution. The percentage contents of various sugar components are shown in Table 5. The percentage content of glucose in the hydrolysate of wild-type oligosaccharide debranching enzyme is 69.30%. The percentage content of glucose in the hydrolysate of the variant V219A is 97.97%, and increased by 28.67%.

TABLE 5

Analysis of products obtained by treatment of tertiary mother liquor with oligosaccharide debranching enzyme

| Components in product | Tertiary mother liquor (%) | Wide type (%) | V219A (%) |
|---|---|---|---|
| G1 | 52.07 | 69.30 | 97.97 |
| G2 | 23.94 | 29.62 | 1.35 |
| IG2 | 13.35 | — | 0.48 |
| G3 | 0.24 | 0.73 | 0.21 |
| P | 8.87 | 0.36 | — |
| IG3 | 0.25 | — | — |
| G4 and higher | 1.28 | — | — |

Note:
G1 to G4 represents glucose, maltose, linear maltotriose, and linear maltotetraose respectively; IG2 to IG3 represents isomaltose, and isomaltotriose respectively; and P represents panose.

Comparative Example. Analysis of Products Obtained with Oligosaccharide Debranching Enzyme Mutant 1 mg/mL panose (pH 6.0) was prepared, the wide type (having an amino acid sequence as shown in SEQ ID NO: 1) or the oligosaccharide debranching enzyme mutant V219A, V219D, V219L, V219T, or V219M was added in an amount of 5 U/g, and the reaction was continued for 24 hrs at 50° C. After the reaction, the enzyme was inactivated by standing in a boiling water bath. The reaction solution was centrifuged at 10,000×g for 5 min, diluted by a certain factor and filtered through a 0.22 m needle filter. Qualitative and quantitative analysis were carried out with G1-G7 over a certain gradient of concentrations mixed with the standard as a control.

The results of product analysis are shown in FIG. 2. The oligosaccharide debranching enzyme mutant V219A catalyzes the hydrolysis of panose to glucose only. The rate of conversion of panose to glucose by the oligosaccharide mutant is 100%. The wild type and other variants catalyze the hydrolysis of panose to glucose and maltose. These suggest that the wide type and V219D, V219L, V219T and V219M mutant cannot hydrolyze the α-1,4-glycosidic bonds of panose, and they can't hydrolyze maltooligosaccharide.

Figure 6:
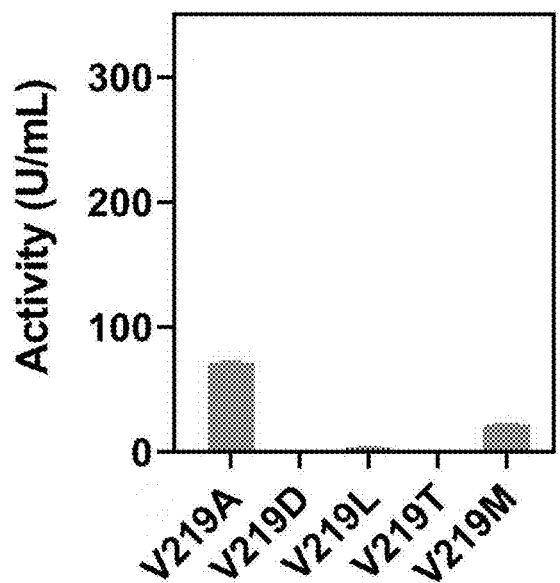
FIG. 6 shows the enzyme activities of various oligosaccharide debranching enzyme mutants.

The enzyme activities of oligosaccharide debranching enzyme mutants V219A, V219D, V219L, V219T, and V219M are shown in FIG. 6.

Apparently, the above-described embodiments are merely examples provided for clarity of description, and are not intended to limit the implementations of the present invention. Other variations or changes can be made by those skilled in the art based on the above description. The embodiments are not exhaustive herein. Obvious variations or changes derived therefrom also fall within the protection scope of the present invention.

What is claimed is:

1. An oligosaccharide debranching enzyme mutant, obtained by mutating valine at position 219 in an amino acid sequence as shown in SEQ ID NO: 1 into alanine.

2. A gene encoding the oligosaccharide debranching enzyme mutant according to claim 1.

3. The gene according to claim 2, having a nucleotide sequence as shown in SEQ ID NO: 2.

4. A recombinant plasmid carrying the gene according to claim 2.

5. A host cell expressing the oligosaccharide debranching enzyme mutant according to claim 1.

6. The cell according to claim 5, wherein the host cell is a bacterial, fungal, plant or animal cell.

7. A method of hydrolyzing an oligosaccharide or producing glucose, comprising: providing the oligosaccharide debranching enzyme mutant according to claim 1; and using the oligosaccharide debranching enzyme mutant in the hydrolysis of the oligosaccharide or the production of glucose.

8. The method according to claim 7, wherein glucose is produced with the oligosaccharide as a substrate, and the oligosaccharide debranching enzyme mutant, or a whole cell or a preparation comprising the mutant as a catalyst.

9. The method according to claim 7, wherein the oligosaccharide comprises linear maltooligosaccharide or iso-maltooligosaccharide.

10. A method for regenerating glucose with a glucose mother liquor, comprising: treating the glucose mother liquor with the oligosaccharide debranching enzyme mutant according to claim 1, or a whole cell or a preparation comprising the mutant.

* * * * *

SEQUENCE LISTING

```
Sequence total quantity: 2
SEQ ID NO: 1            moltype = AA  length = 577
FEATURE                 Location/Qualifiers
source                  1..577
                        mol_type = protein
                        organism = unidentified
SEQUENCE: 1
MLLFPFESRS RSIPTGGWQM KRAWWKESVV YQIYPRSFQD SNGDGIGDIP GIVSRLDYLQ   60
ELGVDVVWLC PVYDSPNDDN GYDIRDYRRI MDEFGTLEDW ERLLEDLHAR GMKLIMDLVV  120
NHSSDEHAWF SESRKSRDGE HRDYYIWRDG KGGAEPNNWS SFFSGSAWKY DGETDQYYLH  180
```

```
LFSSKQPDLN  WENGKVRREV  YNMMAWWLDK  GIDGFRMDVI  NLISKVPGLP  DAPGEGRYRS   240
GADYFMNGPR  VHEYLQEMNR  EVLSRYDIMT  VGETPGVTPE  QAALYVGEDR  GELNMVFQFE   300
HMDIDSGPGG  KWDVQPWRLT  DFKRVMGKWQ  RELQDRGWNS  LYLNNHDQPR  MVSRFGDDKN   360
FRKQSAKMLG  TLLHTLQGTP  YIYQGEELGM  TNVRFGSIED  YRDIETLNMY  KEATGAGRPA   420
EAVMASVYSK  GRDNARTPMQ  WDGSAHGGFT  TGTPWIASNP  NYTEINAEDA  RRDPDSIFHY   480
YRRLIALRKQ  HDVIVYGRYE  ALLEEDERIY  AYTRMLDGER  LLVVLNFFGE  EADCSLPEKI   540
RFESAEPLIG  NYGNGADRDW  RSLKLRPYEA  LVLRLQG                              577

SEQ ID NO: 2            moltype = DNA  length = 1734
FEATURE                 Location/Qualifiers
source                  1..1734
                        mol_type = other DNA
                        organism = synthetic construct
SEQUENCE: 2
atgcttctat ttccatttga gagcaggagc agatccatac cgacaggagg ctggcagatg   60
aagcgagcat ggtggaagga aagcgtcgtc tatcagattt atccccgcag cttccaggac  120
agcaacggag acggcatcgg cgacatcccg ggaatcgttt cccggctgga ttatttgcag  180
gagctcggcg tggatgtcgt ctggctctgt cccgtctatg actccccaa tgacgacaac  240
ggctacgata ttcgcgacta tcggcgcatc atggacgaat tcggcacgct agaggactga  300
gaaaggctgc tggaggatct ccatgcccgc ggcatgaagc tgatcatgga cctcgtcgtg  360
aaccacagct cggacgagca tgcctggttc tcggaatccc gcaagtcccg ggacggcgag  420
catcgcgatt actatatttg gcgggacggc aagggcggag cggagccgaa caactggtcg  480
agcttcttca gcggctccgc atggaaatac gatggggaga cggatcagta ttatctgcat  540
ctgttctcct ccaagcagcc cgatctcaac tgggagaacg ggaaggtccg ccgcgaggtg  600
tacaatatga tggcctggtg gctggacaaa ggcatcgacg gcttccgtat ggacgccatc  660
aacctgatct ccaaggttcc cggactgccg gacgcccccg gagaaggacg gtaccgttcc  720
ggcgccgatt atttcatgaa cggcccgagg gtgcatgagt atttgcagga gatgaaccgc  780
gaggtgctgt cccgctacga catcatgacc gtggggaaga cgccgggcgt gacgccggag  840
caggcggctc tgtacgtcgg cgaggaccgc ggagagctga acatggtgtt tcagttcgag  900
cacatgaaca tcgattccgg acctggcggc aaatggaacg tgcagccttg gaggctgacg  960
gatttcaagc gcgtcatggg caaatggcag cgggagctgc aggacagggg ctggaacagc 1020
ctgtacctga acaatcacga ccagccgcgg atggtgtccc gcttcggcga tgacaagaac 1080
ttccgcaagc agtccgccaa aatgctcggc acgctgctgc acacgctgca gggaacgccc 1140
tacatctatc agggcgagga gctcggcatg accaacgtcc ggttcggctc catcgaggac 1200
taccgggata tcgagacgct gaacatgtac aaggaagcga ccggggccgg acgtcccgcg 1260
gaggctgtca tggcttccgt ctacagcaaa ggaagggaca atgcccgcac gcctatgcag 1320
tgggacggat ccgctcacgg aggcttcacg accggcacgc cgtggatcgc gtccaacccc 1380
aattacacgg agatcaatgc ggaggacgcc cggagagatc cggattccat cttccactac 1440
tatcgcctga tcatcgcgct ccgcaagcag catgacgtca tcgtctacgg caggtacgag 1500
gcgctgctag aggaggacga gcggatctat gcgtatacgc gcatgctgga tggagagcgc 1560
ctgcttgtcg tgctgaactt ctttggagag gaagccgact gcagcttgcc ggagaagata 1620
cgattcgaga gcgccgagcc gctcatcggc aattacggga tggagcgga tagagattgg 1680
cgcagcctga agcttcggcc ttatgaggcg ctcgtcctgc gcttgcaggg ctga         1734
```